US009290559B2

(12) United States Patent
Lim et al.

(10) Patent No.: US 9,290,559 B2
(45) Date of Patent: Mar. 22, 2016

(54) MEMBRANE PROTEIN EXPRESSION VECTOR COMPRISING MAJOR ENVELOPE PROTEIN P9 OF SYSTOVIRUS PHI12 AS A FUSION PARTNER AND METHOD FOR PRODUCING MEMBRANE PROTEIN USING THE SAME

(75) Inventors: Dongbin Lim, Seoul (KR); Yuna Jung, Seoul (KR)

(73) Assignee: Foundation of Soongsil University-Industry Cooperation (KR)

( * ) Notice: Subject to any disclaimer, the term of this patent is extended or adjusted under 35 U.S.C. 154(b) by 3 days.

(21) Appl. No.: 13/885,142

(22) PCT Filed: Nov. 14, 2011

(86) PCT No.: PCT/KR2011/008672
§ 371 (c)(1),
(2), (4) Date: Nov. 19, 2013

(87) PCT Pub. No.: WO2012/064162
PCT Pub. Date: May 18, 2012

(65) Prior Publication Data
US 2014/0065673 A1 Mar. 6, 2014

(30) Foreign Application Priority Data

Nov. 12, 2010 (KR) .................. 10-2010-0112545

(51) Int. Cl.
| | |
|---|---|
| *C07K 14/01* | (2006.01) |
| *C12N 15/86* | (2006.01) |
| *C07K 14/705* | (2006.01) |
| *C07K 14/08* | (2006.01) |
| *C07K 14/005* | (2006.01) |
| *C12N 15/70* | (2006.01) |

(52) U.S. Cl.
CPC ............ *C07K 14/705* (2013.01); *C07K 14/005* (2013.01); *C07K 14/08* (2013.01); *C12N 15/86* (2013.01); *C07K 2319/00* (2013.01); *C07K 2319/03* (2013.01); *C07K 2319/50* (2013.01); *C12N 15/70* (2013.01); *C12N 2720/00022* (2013.01)

(58) Field of Classification Search
CPC ............................... C07K 14/01; C12N 15/86
USPC .............................................. 435/320.1, 69.1
See application file for complete search history.

*Primary Examiner* — Karen Cochrane Carlson
(74) *Attorney, Agent, or Firm* — Fox Rothschild LLP; Peter J. Butch, III; Gunjan Agarwal

(57) ABSTRACT

The present invention relates to an expression vector containing the major envelope protein P9 of Cystovirus phi12 as a fusion partner, and a process for producing a membrane protein using the same. Particularly, the present invention is directed to an expression vector comprising a major envelope protein P9 gene of Cystovirus phi12, a multicloning site (MCS) for inserting a target membrane protein, and a protease recognition site located between a P9 gene and the MCS.

15 Claims, 7 Drawing Sheets

Figure 1
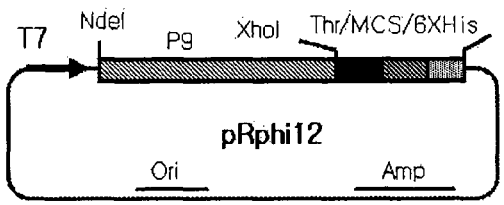
Figure 2
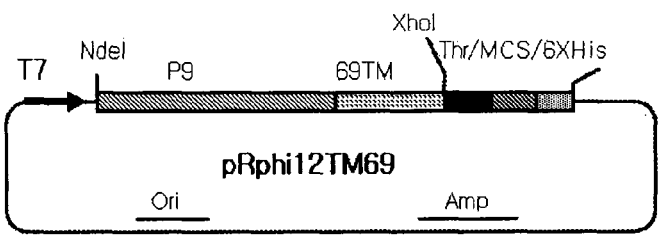
Figure 3

Figure 4

```
pRSET <---: M D N Y K V K V S K A A D G T V S A T A E K R T I G
1           CATATGGATAACTACAAAGTCAAGGTCTGCAAAGCGGCGACGGTACAGTGAGTGCCACCGCAGAGAAAGCCACCATTGG    80
1           GTATACCTATTGATGTTTCAGTTCCAGACGTTTCGCCGCTGCCATGTCACTCACGGTGGCGTCTCTTTCGGTGGTAACC    80
            NdeI

Q A I G D S L T T L I S D D E A S V G Y V K T A V Q
81          TCAAGCAATTGGTGACTCCCTGACCACCCTGATCAGCGACGACGAAGCATCCGTGGGTTACGTCAAGACCGCAGTCCAAG   160
81          AGTTCGTTAACCACTGAGGGACTGGTGGGACTAGTCGCTGCTGCTTCGTAGGCACCCAATGCAGTTCTGGCGTCAGGTTC   160

End of P9<---------:
            A G L V Y G G N L P A K Y E Q T S A P S W N Q L S T R
161         CAGGCTCTGGTGTACGGTGGTATGCTGTTCGCAAAGTACGGTCAAACCAGTGCATTCTCTTGGAACCAGCTCTCGACCCGC   240
161         GTCCGAGACCACATGCCACCATACGACAAGCGTTTCATGGCAGTTTGGTCACGTAAGAGAACCTTGGTCGAGAGCTGGGCG   240

<---------- Extra TM domain from phi6 P9 ----------
            Q E Q A V S V V S W A V A A G L I G E L I G Y R G A R
241         CAAGAGCAGGCCGTTTCGGTTGTGTCATGGGCCGTGGCAGCAGGTCTGATTGGTGAACTGATTGGTTATCGCGGCGCACG    320
241         GTTCTCGTCCGGCAAAGCCAACACAGTACCCGGCACCGTCGTCCAGACTAACCACTTGACTAACCAATAGCGCCGCGTGC    320
                                                                             Thrombin
            ---------------------------------->         * * * */* * recognition site
            S G R K A I L A N I P F L A I S S L V P R G S R A A
321         TTCGGGTCGCAAAGCGATCCTGGCCAACATTCCGTTTCTGGCGATCTCGAGCCTGGTGCCGCGGCTCCCGGGCTGCAG    400
321         AAGCCCAGCGTTTCGCTAGGACCGGTTGTAAGGCAAAGACCGCTAGAGCTCGGACCACGGCGCCGAGGGCCCGACGTC    400
                                                                   XhoI A G T M E A S H H H H H H *     :---> pRSET
401         CTGGTACCATGGAAGCTTCTCACCATCACCATCACCATTAACTTAAGTCGGAGC
401         GACCATGGTACCTTCGAAGAGTGGTAGTGGTAGTGGTAATTGAATTCAGCCTCG    441
```

Figure 5

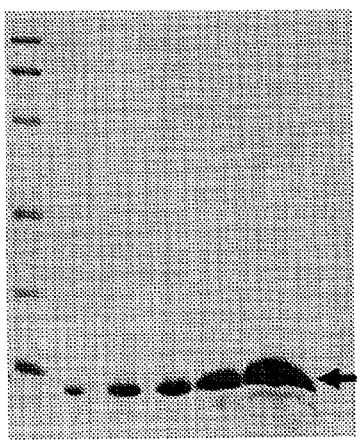

SEQUENCE LISTING

```
<160> NUMBER OF SEQ ID NOS: 33

<210> SEQ ID NO 1
<211> LENGTH: 76
<212> TYPE: PRT
<213> ORGANISM: Artificial
<220> FEATURE:
<223> OTHER INFORMATION: P9 protein of bacteriophage phi12

<400> SEQUENCE: 1

Met Asp Asn Tyr Lys Val Lys Val Ser Lys Ala Ala Asp Gly Thr Val
1               5                   10                  15

Ser Ala Thr Ala Glu Lys Arg Thr Ile Gly Gln Ala Ile Gly Asp Ser
            20                  25                  30

Leu Thr Thr Leu Ile Ser Asp Asp Glu Ala Ser Val Gly Tyr Val Lys
        35                  40                  45

Thr Ala Val Gln Ala Gly Leu Val Tyr Gly Gly Met Leu Phe Ala Lys
    50                  55                  60

Tyr Arg Gln Thr Ser Ala Phe Ser Trp Asn Pro Leu
65                  70                  75

<210> SEQ ID NO 2
<211> LENGTH: 120
<212> TYPE: PRT
<213> ORGANISM: Artificial
<220> FEATURE:
<223> OTHER INFORMATION: Sequence of pRphi12TM69

<400> SEQUENCE: 2

Met Asp Asn Tyr Lys Val Lys Val Ser Lys Ala Ala Asp Gly Thr Val
1               5                   10                  15

Ser Ala Thr Ala Glu Lys Arg Thr Ile Gly Gln Ala Ile Gly Asp Ser
            20                  25                  30

Leu Thr Thr Leu Ile Ser Asp Asp Glu Ala Ser Val Gly Tyr Val Lys
        35                  40                  45

Thr Ala Val Gln Ala Gly Leu Val Tyr Gly Gly Met Leu Phe Ala Lys
    50                  55                  60

Tyr Arg Gln Thr Ser Ala Phe Ser Trp Asn Pro Leu Ser Thr Arg Gln
65                  70                  75                  80

Glu Gln Ala Val Ser Val Val Ser Trp Ala Val Ala Ala Gly Leu Ile
                85                  90                  95

Gly Glu Leu Ile Gly Tyr Arg Gly Ala Arg Ser Gly Arg Lys Ala Ile
            100                 105                 110

Leu Ala Asn Ile Pro Phe Leu Ala
        115                 120

<210> SEQ ID NO 3
<211> LENGTH: 236
<212> TYPE: DNA
<213> ORGANISM: Artificial
<220> FEATURE:
```

<223> OTHER INFORMATION: Synthetic P9 protein of bacteriophage phi12

<400> SEQUENCE: 3

```
catatggata actacaaagt caaggtctcc aaagcggccg acggtacagt gagtgccacc      60
gcagagaaac gcaccattgg tcaagcaatt ggtgactccc tgaccaccct gatcagcgac     120
gacgaagcat ccgtgggtta cgtcaagacc gcagtccaag caggtctggt gtacggtggt     180
atgctgttcg caaagtaccg tcaaaccagt gcattctctt ggaacccgct ctcgag         236
```

<210> SEQ ID NO 4
<211> LENGTH: 371
<212> TYPE: DNA
<213> ORGANISM: Artificial
<220> FEATURE:
<223> OTHER INFORMATION: Sequence of pRphi12TM69

<400> SEQUENCE: 4

```
catatggata actacaaagt caaggtctcc aaagcggccg acggtacagt gagtgccacc      60
gcagagaaac gcaccattgg tcaagcaatt ggtgactccc tgaccaccct gatcagcgac     120
gacgaagcat ccgtgggtta cgtcaagacc gcagtccaag caggtctggt gtacggtggt     180
atgctgttcg caaagtaccg tcaaaccagt gcattctctt ggaacccgct ctcgaccgc      240
caagagcagg ccgtttcggt tgtgtcatgg gccgtggcag caggtctgat tggtgaactg     300
attggttatc gcggcgcacg ttcgggtcgc aaagcgatcc tggccaacat tccgtttctg     360
gcgatctcga g                                                         371
```

<210> SEQ ID NO 5
<211> LENGTH: 441
<212> TYPE: DNA
<213> ORGANISM: Artificial
<220> FEATURE:
<223> OTHER INFORMATION: P9+TM+Thrombin site+MCS+His tag

<400> SEQUENCE: 5

```
catatggata actacaaagt caaggtctcc aaagcggccg acggtacagt gagtgccacc      60
gcagagaaac gcaccattgg tcaagcaatt ggtgactccc tgaccaccct gatcagcgac     120
gacgaagcat ccgtgggtta cgtcaagacc gcagtccaag caggtctggt gtacggtggt     180
atgctgttcg caaagtaccg tcaaaccagt gcattctctt ggaacccgct ctcgaccgc      240
caagagcagg ccgtttcggt tgtgtcatgg gccgtggcag caggtctgat tggtgaactg     300
attggttatc gcggcgcacg ttcgggtcgc aaagcgatcc tggccaacat tccgtttctg     360
gcgatctcga gcctggtgcc gcgcggctcc cgggctgcag ctggtaccat ggaagcttct     420
caccatcacc atcaccatta a                                              441
```

<210> SEQ ID NO 6
<211> LENGTH: 32
<212> TYPE: DNA
<213> ORGANISM: Artificial
<220> FEATURE:
<223> OTHER INFORMATION: Synthetic primer: Adora

<400> SEQUENCE: 6

```
aagctgcaga tatccccaac aacagcactg ct                                   32
```

<210> SEQ ID NO 7
<211> LENGTH: 31
<212> TYPE: DNA
<213> ORGANISM: Artificial

```
<220> FEATURE:
<223> OTHER INFORMATION: Synthetic primer: Adora

<400> SEQUENCE: 7
ggggtaccaa ttgctactca gaattcttct c                              31

<210> SEQ ID NO 8
<211> LENGTH: 28
<212> TYPE: DNA
<213> ORGANISM: Artificial
<220> FEATURE:
<223> OTHER INFORMATION: Synthetic primer: Endo

<400> SEQUENCE: 8
tgaccagctg aaaccctttg cctcaggg                                  28

<210> SEQ ID NO 9
<211> LENGTH: 30
<212> TYPE: DNA
<213> ORGANISM: Artificial
<220> FEATURE:
<223> OTHER INFORMATION: Synthetic primer: Endo

<400> SEQUENCE: 9
agctaagctt ggttcatgct gtccttatgg                                30

<210> SEQ ID NO 10
<211> LENGTH: 32
<212> TYPE: DNA
<213> ORGANISM: Artificial
<220> FEATURE:
<223> OTHER INFORMATION: Synthetic primer: Lyso

<400> SEQUENCE: 10
tgaccagctg ctgccatctc tacttccatc cc                             32

<210> SEQ ID NO 11
<211> LENGTH: 30
<212> TYPE: DNA
<213> ORGANISM: Artificial
<220> FEATURE:
<223> OTHER INFORMATION: Synthetic primer: Lyso

<400> SEQUENCE: 11
agctaagctt gaaccacaga gtggtcattg                                30

<210> SEQ ID NO 12
<211> LENGTH: 29
<212> TYPE: DNA
<213> ORGANISM: Artificial
<220> FEATURE:
<223> OTHER INFORMATION: Synthetic primer: Dopa

<400> SEQUENCE: 12
cccgggtgga tccactgaat ctgtcctgg                                 29

<210> SEQ ID NO 13
<211> LENGTH: 28
<212> TYPE: DNA
<213> ORGANISM: Artificial
<220> FEATURE:
<223> OTHER INFORMATION: Synthetic primer: Dopa

<400> SEQUENCE: 13
aagcttcgca gtggaggatc ttcaggaa                                  28
```

<210> SEQ ID NO 14
<211> LENGTH: 29
<212> TYPE: DNA
<213> ORGANISM: Artificial
<220> FEATURE:
<223> OTHER INFORMATION: Synthetic primer: Leuko

<400> SEQUENCE: 14
cccgggacga tgaaacagga aatctgaca                              29

<210> SEQ ID NO 15
<211> LENGTH: 28
<212> TYPE: DNA
<213> ORGANISM: Artificial
<220> FEATURE:
<223> OTHER INFORMATION: Synthetic primer: Leuko

<400> SEQUENCE: 15
aagcttctac tttacatatt tcttctcc                               28

<210> SEQ ID NO 16
<211> LENGTH: 29
<212> TYPE: DNA
<213> ORGANISM: Artificial
<220> FEATURE:
<223> OTHER INFORMATION: Synthetic primer: MC1R

<400> SEQUENCE: 16
gatatcctgc tgtgcaggga tcccagaga                              29

<210> SEQ ID NO 17
<211> LENGTH: 28
<212> TYPE: DNA
<213> ORGANISM: Artificial
<220> FEATURE:
<223> OTHER INFORMATION: Synthetic primer: MC1R

<400> SEQUENCE: 17
aagcttccca ggagcacgtc agcacctc                               28

<210> SEQ ID NO 18
<211> LENGTH: 29
<212> TYPE: DNA
<213> ORGANISM: Artificial
<220> FEATURE:
<223> OTHER INFORMATION: Synthetic primer: Prost

<400> SEQUENCE: 18
gatatcacaa ggagacccgg ggctacgga                              29

<210> SEQ ID NO 19
<211> LENGTH: 28
<212> TYPE: DNA
<213> ORGANISM: Artificial
<220> FEATURE:
<223> OTHER INFORMATION: Synthetic primer: Prost

<400> SEQUENCE: 19
aagcttcatt tccccaaaat tcctcttg                               28

<210> SEQ ID NO 20
<211> LENGTH: 29
<212> TYPE: DNA
<213> ORGANISM: Artificial
<220> FEATURE:
<223> OTHER INFORMATION: Synthetic primer: Neuro

```
<400> SEQUENCE: 20
atgacaatat tcaacattat tttcccagg                                       29

<210> SEQ ID NO 21
<211> LENGTH: 32
<212> TYPE: DNA
<213> ORGANISM: Artificial
<220> FEATURE:
<223> OTHER INFORMATION: Synthetic primer: Neuro

<400> SEQUENCE: 21
agctaagctt gattttttca ttatcatcat tg                                   32

<210> SEQ ID NO 22
<211> LENGTH: 27
<212> TYPE: DNA
<213> ORGANISM: Artificial
<220> FEATURE:
<223> OTHER INFORMATION: Synthetic primer: ThiaT

<400> SEQUENCE: 22
gacagctgat gtgcccggcc cggtgtc                                         27

<210> SEQ ID NO 23
<211> LENGTH: 30
<212> TYPE: DNA
<213> ORGANISM: Artificial
<220> FEATURE:
<223> OTHER INFORMATION: Synthetic primer: ThiaT

<400> SEQUENCE: 23
ggaagcttct gaagtggtta cttgagaact                                      30

<210> SEQ ID NO 24
<211> LENGTH: 28
<212> TYPE: DNA
<213> ORGANISM: Artificial
<220> FEATURE:
<223> OTHER INFORMATION: Synthetic primer: Sero

<400> SEQUENCE: 24
gacagctgtg ctgctgtggg tccagcag                                        28

<210> SEQ ID NO 25
<211> LENGTH: 30
<212> TYPE: DNA
<213> ORGANISM: Artificial
<220> FEATURE:
<223> OTHER INFORMATION: Synthetic primer: Sero

<400> SEQUENCE: 25
ggaagcttca gcgtactgcc agatggacca                                      30

<210> SEQ ID NO 26
<211> LENGTH: 28
<212> TYPE: DNA
<213> ORGANISM: Artificial
<220> FEATURE:
<223> OTHER INFORMATION: Synthetic primer: Glut4

<400> SEQUENCE: 26
gagatatctg ccgtcgggtt tccagcag                                        28

<210> SEQ ID NO 27
```

<211> LENGTH: 30
<212> TYPE: DNA
<213> ORGANISM: Artificial
<220> FEATURE:
<223> OTHER INFORMATION: Synthetic primer: Glut4

<400> SEQUENCE: 27
ggaagcttcg tcattctcat ctggccctaa                                              30

<210> SEQ ID NO 28
<211> LENGTH: 29
<212> TYPE: DNA
<213> ORGANISM: Artificial
<220> FEATURE:
<223> OTHER INFORMATION: Synthetic primer: mPGES

<400> SEQUENCE: 28
gacagctgtg cctgcccaca gcctggtga                                               29

<210> SEQ ID NO 29
<211> LENGTH: 30
<212> TYPE: DNA
<213> ORGANISM: Artificial
<220> FEATURE:
<223> OTHER INFORMATION: Synthetic primer: mPGES

<400> SEQUENCE: 29
ggaagcttcc aggtggcggg ccgcttccca                                              30

<210> SEQ ID NO 30
<211> LENGTH: 30
<212> TYPE: DNA
<213> ORGANISM: Artificial
<220> FEATURE:
<223> OTHER INFORMATION: Synthetic primer: Musc

<400> SEQUENCE: 30
gatatcccaa cacttcagcc ccacctgctg                                              30

<210> SEQ ID NO 31
<211> LENGTH: 29
<212> TYPE: DNA
<213> ORGANISM: Artificial
<220> FEATURE:
<223> OTHER INFORMATION: Synthetic primer: Musc

<400> SEQUENCE: 31
aagcttcgca ttggcgggag ggagtgcgg                                               29

<210> SEQ ID NO 32
<211> LENGTH: 28
<212> TYPE: DNA
<213> ORGANISM: Artificial
<220> FEATURE:
<223> OTHER INFORMATION: Synthetic primer: P2X

<400> SEQUENCE: 32
gagatatctg gcgggctgct gcgccgcg                                                28

<210> SEQ ID NO 33
<211> LENGTH: 30
<212> TYPE: DNA
<213> ORGANISM: Artificial
<220> FEATURE:

-continued

```
<223> OTHER INFORMATION: Synthetic primer: P2X

<400> SEQUENCE: 33
ggaagcttcc tggtccagct cactagcaag                                        30
```

MEMBRANE PROTEIN EXPRESSION VECTOR COMPRISING MAJOR ENVELOPE PROTEIN P9 OF SYSTOVIRUS PHI12 AS A FUSION PARTNER AND METHOD FOR PRODUCING MEMBRANE PROTEIN USING THE SAME

The present application is the U.S. National Phase of International Patent Application Serial No. PCT/KR2011/008672, filed Nov. 14, 2011, which claims priority to Korean Patent Application Serial No. 10-2010-0112545, filed Nov. 12, 2010. The foregoing applications are hereby incorporated by reference in their entireties.

TECHNICAL FIELD

The present invention relates to an expression vector containing the major envelope protein P9 of Cystovirus phi12 as a fusion partner, and a process for producing a membrane protein using the same. Particularly, the present invention is directed to an expression vector comprising a major envelope protein P9 gene of Cystovirus phi12, a multicloning site (MCS) for inserting a target membrane protein, and a protease recognition site located between a P9 gene and the MCS.

BACKGROUND ART

Membrane proteins constitute about 25-30% of the proteome of an organism and participate in basic energy metabolisms such as respiration or photosynthesis, communication between a cell and a cell or between a cell and the outside, material transfer, lipid metabolism, etc. In addition, it was reported that about 50% of commercially available drugs act on a G-protein coupled receptor (GPCR), a kind of membrane proteins, as a working point (Lundstrom, K., Bioorg. Med. Chem. Lett., 15:3654, 2005), and working points of ¼ of the top-selling 100 drugs are GPCR (Klabunde, T. and Hessler, G., ChemBioChem. 3:928-944, 2002).

However, researches for the functions and structures of membrane proteins fall behind those of water-soluble proteins although membrane proteins are economically important. This is because, unlike water-soluble proteins, it is almost impossible to produce membrane proteins, especially multipass transmembranes, by recombinant DNA techniques (Mancia F. and Hendrickson W. A, Mol. BioSyst. 3:723-734, 2007).

Therefore, unlike water-soluble proteins, it is extremely unusual to express membrane proteins by using microorganisms and, moreover, the amount of expressed membrane proteins is very small (Marullo, S. et al., Proc. Natl. Acd. Sci. USA., 85:7551, 1988; Grisshammer et al. Biochem J., 295:571, 1993). It was reported that about 3 mg per 100 g of *E. coli* cells were obtained through expression of fusion form of a neurotensin receptor and a maltose binding protein, which is the especially successful case (White, J. F., et al. FEBS Lett. 564:289, 2004).

However, when the expression of foreign membrane protein is induced through *E. coli*, hosts become dead before the expression of the target protein is observed. In order to solve this problem, the mutant *E. coli* C41 and C43 were developed, which do not die due to inducing expression of membrane protein after introducing a membrane protein expression vector (Miroux, B. and Walker, J. E., J. Mol. Biol., 260:289-298, 1996), and the *E. coli* C41 (DE3) and C43 (DE3) had been used for expression of a membrane protein (Korepanova, A., et al., Protein Science, 14:148-158, 2005).

In addition, it was reported that multi-membrane proteins of eukaryotic cells can be expressed by using proteins of *Bacillus subtilus*, called as Mistic, as a fusion partner and, however, it was not effective in expression of membrane proteins (Roosild T. P. et al., Science, 307:1317-1321, 2005; Wagner et al., Trends in Biotech., 24:364-371, 2006). Recently, human membrane proteins, such as occluding, claudin 4, ferric reductase and potassium channel, were expressed by using *E. coli* GlpF (glycerol-conducting channel protein) as a fusion partner and, however, this method cannot be applicable when an amino end of a target protein is outside a cell membrane and, in addition, the amount of expression was very small (Neophytou, I. et al., Appl. Microbiol. Biotechnol., 77:375-381, 2007).

Moreover, development of an expression system by using yeasts which have well-developed intracellular membrane systems, has been attempted. Recently, a method for deciding whether or not a membrane protein is expressed by checking the fluorescence of green fluorescent protein (GFP) after inserting a target protein, as a fusional protein with GFP, into a yeast expression vector by using GFP as an expression reporter, was developed (Osterberg M. et al., Proc. Natl. Acad. Sci., 103:11148-11153, 2006; Newstead S. et al., Proc. Natl. Acad. Sci., 104:13936-13941, 2007). In this case, the expression rate of proteins derived from animals including a human was very low and the amount of expression thereof was also very small, while the expression rate of yeast-derived proteins was high.

The present inventors has researched into a method for effective expression of membrane proteins of eukaryotic and prokaryotic cells and finally completed the present invention, a method for effective expression of a target membrane protein by combining Cystovirus phi12, a fusion partner, with a major envelope protein P9.

DISCLOSURE

Technical Problem

The primary object of the present invention is to provide an expression vector comprising a major envelope protein P9 gene of Cystovirus phi12, a multicloning site (MCS) for inserting a target membrane protein, and a protease recognition site located between a P9 gene and the MCS.

Another object of the present invention is to provide a cell transformed by the expression vector of the membrane proteins of the present invention.

Further object of the present invention is to provide a process for producing a target membrane protein comprising inserting a gene encoding the target membrane protein into the MCS of the expression vector of the present invention, transforming said gene into a cell, and culturing the transformed cell.

Technical Solution

The afore-mentioned primary object of the present invention can be achieved by providing an expression vector comprising a major envelope protein P9 gene of Cystovirus phi12, a multicloning site (MCS) for inserting a target membrane protein, and a protease recognition site located between a P9 gene and the MCS.

The expression vector according to the present invention is characterized by overexpression of a target membrane protein by using a major envelope protein P9 of Cystovirus phi12 as a fusion partner, and comprises a gene which is joined at and encodes the target membrane protein at 5'-end or 3'-end of the P9 protein encoding gene, thereby expressing the fusion protein which is fused by the target protein at N-terminal or C-terminal of the P9 protein. Preferably, pRphi12 may be used as the expression vector.

The fusion protein which is fused by the target protein at N-terminal or C-terminal of the P9 protein is expressed by adding extra transmembrane domain of other proteins to the C-terminal of the P9 protein, followed by linking a gene encoding the target membrane protein at 5'-terminal or 3'-terminal of the fusion protein.

The envelope protein P9 may have an amino acid sequence of SEQ ID NO: 1 (P9) or SEQ ID NO: 2 (P9+TM) and, however, any substitution, addition or deletion of amino acids in the amino acid sequences without influencing the functions of the proteins and, moreover, a part of the proteins may be used or a specific domain may be repeatedly used, as intended. These modified amino acid sequences are also included within the scope of the present invention. Therefore, polypeptides which have substantially the same amino acid sequence as the above-mentioned proteins, and fragments thereof may be used in the present invention, where the substantially the same peptide refers to any peptide having a sequence homology of preferably more than or equal to 80%, more preferably more than or equal to 90% and most preferably more than or equal to 95%.

The gene encoding the envelope protein P9 includes base sequences derived from the amino acid sequences of the protein, according to the genetic code, optimizes codons so as for the genes to be properly expressed in the selected host. Typical examples of these genes include a base sequence of SEQ ID NO: 3 (P9) or SEQ ID NO: 4 (P9+TM). The base sequences of SEQ ID NO: 3 and SEQ ID NO: 4 encode the amino acid sequences of SEQ ID NO: 1 and SEQ ID NO: 2, respectively.

The expression vector of the present invention may comprise a protease recognition site and a suitable linker DNA which are located between the envelope protein P9 and the site into which a target protein is to be inserted. For example, the expression vector of the present invention may comprise, in the direction of 5' to 3', a promoter, a gene encoding the envelope protein P9 of Cystovirus phi12, a protease recognition site, a multicloning site (MCS) into which a target protein gene is to be inserted, and a histidin tag, as translational fusion form. In addition, the expression vector of the present invention may additionally comprise an antibiotic resistant gene, if necessary.

Furthermore, the expression vector of the present invention may additionally comprise an extra transmembrane (TM) domain between the envelope protein P9 and the protease recognition site. The extra TM domain which may be added to the expression vector of the present invention may be any TM domain known in the art, for example, a protein P9 of Cystovirus, a protein P10 of Cystovirus, a major coat protein of *Pseudomonas* phage Pf3, or a major coat protein of Bacteriophage M13. Preferably, pRphi12TM69 comprising TM domain of P9 protein of Cystovirus phi6 may be used as an expression vector.

In the expression vector of the present invention, the promoter may be T7 promoter, T5 promoter or tac promoter and, however, it is evident for a person skilled in the art that any other suitable promoter which can satisfactorily produce a target protein in the selected host cell. Moreover, the protease may be thrombin, Tev or enterokinase.

In addition, the present invention provides a gene which is manipulated for expressing a target protein as one polypeptide by being fused with a fusion partner derived from Cystovirus. This manipulated fusion gene may produce the target protein by being introduced into bacteria in the form of episome or in the form inserted into a chromosome, or by cell-free protein synthesis in vitro without introducing within a cell.

According to the present invention, the membrane protein may be selected from the group consisting of a membrane receptor, an ion channel, a membrane transporter, a pump, a membrane enzyme, a ligand and a receptor for intercellular communication, a linker for linking cells, a membrane vesicle for intracellular material transport, a ligand and a receptor of endo- and exo-cytosis, a biomembrane protein relating to a viral life cycle, an antibody or a part thereof, and a toxoprotein. For example, the membrane protein may be a human multi-membrane G-protein coupled receptor (GPCR) such as A3 adenosine receptor (Adora: Genbank Accession No. NM_000677), endothelin receptor type A (Endo; Genbank Accession No. BC022511), lysophosphatidic acid receptor 2 (Lyso; Genbank Accession No. BC030615), dopamine receptor D2 (Dopa; Genbank Accession No. BC021195), cysteinyl leukotriene receptor 1 (Leuko; Genbank Accession No. BC035750), melanocortin 1 receptor (MC1R; Genbank Accession No. NM_002386), prostaglandin E receptor 3 (Prost; Genbank Accession No. BC024229), neuropeptide Y receptor Y1 (Neuro; Genbank Accession No. BC036657), a solute carrier such as thiamine transporter (ThiaT; Genbank Accession No. BC018514), a solute carrier such as facilitated glucose transporter member 4 (GLUT4; Genbank Accession No. BC014282), a gated ion channel such as serotonin receptor (5-hydroxytryptamine receptor 3A, Sero; Genbank Accession No. BC004453), muscarinic acetylcholine receptor (Musc; Genbank Accession No. NM000738), purinergic receptor P2X4 (P2X4; Genbank Accession No. BC033826), or a biomembrane enzyme such as prostaglandin E synthase (mPGES; Genbank Accession No. BC004878).

Another object of the present invention can be achieved by providing a cell transformed by the expression vector of the membrane proteins of the present invention.

The cell may be microorganisms such as bacteria, for example, *E. coli, Pseudomonas aeruginosa, Bacillus subtilis*, etc., or animal cells such as yeast.

According to one embodiment of the present invention, the expression vector pRphi12TM69 comprising, as a fusion partner, a major envelope protein P9 having an amino acid sequence of SEQ ID NO: 1 and an extra transmembrane domain of phi6 P9 was produced (FIGS. 1 and 2) and, then, *E. coli* BL21 (DE3) was transformed by using the pRphi12TM69. The transformed *E. coli* strain was named as XL1blue/pRphi12TM69 and was deposited to the Korean Collection for Type Cultures on Oct. 1, 2010 as the accession number KCTC 11769BP.

Further object of the present invention can be achieved by providing a process for producing a target membrane protein comprising inserting a gene encoding the target membrane protein into the MCS of the expression vector of the present invention, transforming said gene into a cell, and culturing the transformed cell.

In addition, the present invention provides a process for producing a target membrane protein comprising inserting a DNA encoding the target membrane protein into the MCS of the expression vector of the present invention, transforming said gene into a cell, and culturing the transformed cell.

According to one embodiment of the present invention, various eukaryote-derived target membrane proteins were inserted into the MCS of the expression vector pRphi12TM69 and, then, induced to be overexpressed in *E. coli* (FIGS. 8 and 9), and it was examined by GFP fusion that the overexpressed proteins were normally folded. The overexpressed proteins were well extracted by using a moderate solvent such as LDAO (lauryldimethylamine oxide) (FIG. 15). By purifying these overexpressed proteins through Ni-NTA column, it was ascertained that various membrane proteins can be efficiently expressed and purified by using the expression vector of the present invention.

Although the embodiment of the present invention was carried out by using bacteriophage phi12, it is evident to a person skilled in the art that similar results may be obtained by using a major envelope protein P9 of other bacteriophages which fall under Cystovirus, for example, phi8, phi13, etc. In addition, although E. coli was used as a host cell in the embodiment of the present invention, it is also apparent that other bacteria such as Bacillus subtilis and Pseudomonas aeruginosa may be used as a host cell.

Additionally, a cell which is produced by the process of the present invention and a target protein is expressed therein, may be utilized for a process for measurement of a membrane protein activity characterized in that such cell is used, and for development of a detection system of ligand-receptor binding.

In addition, antibodies may be produced by recovering the antibodies formed from the immunoreaction induced by administrating a fusion protein of the P9 protein-target protein, or only a target protein expressed within a biomembrane through the expression vector of the present invention and the target protein, to a vertebrate animal.

Advantageous Effects

Since membrane proteins can be effectively overexpressed by using the membrane protein expression vector of the present invention comprising an envelope protein P9 of Cystovirus phi12 as a fusion partner, the expression vector may be used for development of pharmaceutical agents acting on membrane proteins, biotransformation by using membrane enzymes, etc.

DESCRIPTION OF DRAWINGS

FIG. 1 shows the structure of the membrane protein expression vector pRphi12 according to the present invention.

FIG. 2 shows the structure of the membrane protein expression vector pRphi12TM69 according to the present invention.

FIG. 3 shows the base sequence list and amino acid sequence list of the P9 protein and the linker-inserted portion out of the expression vector pRphi12.

FIG. 4 shows the base sequence list and amino acid sequence list of the P9 protein, an extra transmembrane (TM) domain derived from P9 of phi6, and the linker-inserted portion out of the expression vector pRphi12TM69.

FIG. 5 shows the results of purification of the P9 of phi12 by using the expression vector pRphi12.

BEST MODE

Hereinafter, the present invention will be described in greater detail with reference to the following examples. The examples are given only for illustration of the present invention and not to be limiting the present invention.

Example 1

Production of Recombinant Vector Overexpressing P9 of Cystovirus Phi12

In order to produce a recombinant vector overexpressing P9 of Cystovirus phi6, total gene of SEQ ID NO: 3 which encodes the major envelope protein P9 (SEQ ID NO: 1) of phage phi12 was synthesized. At this time, the codons of the synthesized gene were optimized for E. coli. The recognition sequence of the restriction enzyme NdeI was inserted near the initiation codon and the recognition sequence of the restriction enzyme XhoI was inserted into the site where the termination codon was removed. In addition, a DNA fragment was synthesized such that a base sequence encoding a thrombin recognition site, MCS, six His codons and a termination codon were positioned next to XhoI in order (refer to SEQ ID NO: 5), and then was inserted into NdeI/HindIII site of a commercially available expression vector pRSET A (Invitrogen), thereby producing the recombinant vector having the structure of FIG. 1. These vectors were named as "pRphi12."

In addition, DNA corresponding to the transmembrane domain of the P9 protein of Cystovirus phi6 was synthesized and, then, inserted at the site of XhoI of pRphi12, thereby producing the vector pRphi12TM69 shown in FIG. 2 (SEQ ID NO: 2 and 4). E. coli BL21 strain (DE3) was transformed by the vector pRphi12TM69 and the transformed E. coli was named as "XL1blue/pRphi12TM69" which was deposited to the Korean Collection for Type Cultures on Oct. 1, 2010 as the accession number KCTC 11769BP. A Viability statement issued pursuant to Rule 10.2 by the Korean Collection for Type Cultures (KCTC) under the International Depository Authority clearly shows that: (1) The deposit for E. Coli XL1-blue/pRphi12TM69 was made on Oct. 1, 2010, where it was given accession number KCTC 11769BP, (2) The above mentioned E. Coli XL1-blue/pRphi12TM69 was found viable on Apr. 17, 2015, and (3) The above-mentioned E. coli XL1-blue/pRphi12TM69 will be available to the public under the conditions specified in 37 C.F.R. §1.801-809. Specifically, the instant invention will be irrevocably and without restriction released to the public upon the issuance of a patent. Access to the deposit will be available during pendency of the above-captioned patent Application to those determined by the Director to be entitled thereto under 37 C.F.R. §1.13 and 35 U.S.C. §122.

Example 2

Purification of the Protein P9 of the Phage Phi12 and Production of Antibodies

Figure 6:
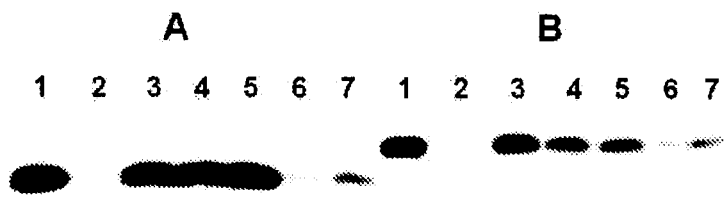
FIG. 6 shows that P9 and P9-TM fusions produced by the expression vectors pRphi12 and pRphi12TM69 are present in cell membranes and are extracted by LDAO and Triton X100.

The transformed *E. coli* produced in Example 1 was sonicated and centrifuged at 12,000 rpm (high speed centrifuge) to obtain the supernatant. Then, the supernatant was centrifuged at 50,000 rpm (ultracentrifuge, 100,000 g) to obtain a precipitate containing cell membrane fragments. Tris-HCl buffer solution (pH 7.5) containing 39 mM LDAO was added to the precipitate and the precipitate was suspended. Then, the suspension was centrifuged at 50,000 rpm and the supernatant was obtained. P9 protein containing His-tag and thrombin recognition site was purified by Ni-NTA-affinity chromatography (Column: His TrapTM HP (GE Healthcare); mobile phase: 20 mM Tris-HCl buffer solution (pH 7.5) containing 39 mM LDAO; concentration gradient of imidazole: 20~500 mM) and then Superose 6 gel filtration (Column: SuperdexTM 75 10/300 GL (GE Healthcare); mobile phase: 20 mM Tris-HCl buffer solution (pH 7.5) containing 13 mM LDAO) (FIG. 5). Then, antibody was generated by injection of the thus purified P9 into mice. FIG. 6 shows immunoblot results that fusion partners generated by pRphi12 and pRphi12TM69, with use of the thus prepared antibodies, are present in cell membranes and are extracted with LDAO and Triton X100.

Example 3

Production of Plasmids Expressing Human Membrane Proteins by Expression Vectors pRphi12 and pRphi12TM69

(Adora, Endo, Lyso). cDNAs encoding A3 adenosine receptor (Adora: Genbank Accession No. NM_000677), endothelin receptor type A (Endo; Genbank Accession No. BC022511) and lysophosphatidic acid receptor 2 (Lyso; Genbank Accession No. BC030615), which are human GPCRs, were used as templates; SEQ ID NO: 6 and 7, SEQ ID NO: 8 and 9, and SEQ ID NO: 10 and 11 were used as primers for Adora, Endo and Lyso, respectively; and then PCR was performed (94° C. and 3 min, 94° C. and 1 min, 55° C. and 1 min, 72° C. and 1 min, 25 cycles, then 72° C. and 10 min for Adora; 94° C. and 3 min, 94° C. and 1 min, 60° C. and 1 min, 72° C. and 1 min, 25 cycles, then 72° C. and 10 min for Endo and Lyso). The amplified DNA of Adora was cut by restriction enzymes EcoRV and EcoRI, and the amplified DNAs of Endo and Lyso were cut by restriction enzymes PvuII and HindIII, and then the thus obtained DNA fragments were inserted into restriction sites of pRphi12 and pRphi12TM69 (SmaI/EcoRI for Adora, SmaI/HindIII for Endo and Lyso), thereby producing human GPCR protein expression plasmids.

(Dopa, Leuko, Melano, Prostag). cDNAs encoding dopamine receptor D2 (Dopa; Genbank Accession No. BC021195), cysteinyl leukotriene receptor 1 (Leuko; Genbank Accession No. BC035750), melanocortin 1 receptor (MC1R; Genbank Accession No. NM_002386) and prostaglandin E receptor 3 (Prost; Genbank Accession No. BC024229), which are human GPCRs, were used as templates; suitable oligomers (SEQ ID NO: 12 and 13 for Dopa, SEQ ID NO: 14 and 15 for Leuko, SEQ ID NO: 16 and 17 for MC1R, and SEQ ID NO: 18 and 19 for Prost) were used as primers; and then PCR was performed (94° C. and 3 min, 94° C. and 1 min, 60° C. and 1 min, 72° C. and 1 min, 28 cycles, then 72° C. and 10 min). The amplified DNAs were cut by suitable restriction enzymes SmaI/HindIII for Dopa and Leuko, and EcoRV/HindIII for Melano and Prostag) and, then, each of the thus obtained DNA fragments was inserted into the restriction site (SmaI/HindIII) of pRphi12 and pRphi12TM69, thereby producing human multimembrane protein expression plasmids.

(Neuro, ThiaT, Sero). cDNAs encoding a human multimembrane protein such as neuropeptide Y receptor Y1 (Neuro; Genbank Accession No. BC036657), a solute carrier such as thiamine transporter (ThiaT; Genbank Accession No. BC018514) and a gated ion channel such as serotonin receptor (5-hydroxytryptamine receptor 3A, Sero; Genbank Accession No. BC004453), were used as templates; SEQ ID NO: 20 and 21, SEQ ID NO: 22 and 23, and SEQ ID NO: 24 and 25 were used as primers for Neuro, ThiaT and Sero, respectively; and then PCR was performed (94° C. and 3 min, 94° C. and 1 min, 63° C. and 1 min, 72° C. and 1 min, 25 cycles, then 72° C. and 10 min). The amplified DNAs of Neuro, ThiaT and Sero were cut by restriction enzymes SspI/HindIII, PvuII/HindIII and PvuII/HindIII, respectively, and then each of the thus obtained DNA fragments was inserted into the restriction site (SmaI/HindIII) of pRphi12 and pRphi12TM69, thereby producing human multimembrane protein expression plasmids.

(Glut4, mPGES). cDNAs encoding a solute carrier such as facilitated glucose transporter member 4 (GLUT4; Genbank Accession No. BC014282), and a biomembrane enzyme such as prostaglandin E synthase (mPGES; Genbank Accession No. BC004878), were used as templates; SEQ ID NO: 26 and 27, and SEQ ID NO: 28 and 29 were used as primers for GLUT4 and mPGES, respectively; and then PCR was performed (94° C. and 3 min, 94° C. and 1 min, 60° C. and 1 min, 72° C. and 1 min, 25 cycles, then 72° C. and 10 min for GLUT4; 94° C. and 3 min, 94° C. and 1 min, 65° C. and 1 min, 72° C. and 1 min, 25 cycles, then 72° C. and 10 min for mPGES). The amplified DNAs of GLUT4 and mPGES were cut by the restriction enzymes EcoRV/HindIII and PvuII/HindIII, respectively, and then each of the thus obtained DNA fragments was inserted into the restriction site (SmaI/HindIII) of pRphi12 and pRphi12TM69, thereby producing human multi-membrane protein expression plasmids.

cDNAs encoding an ion channel such as muscarinic acetylcholine receptor (Musc; Genbank Accession No. NM_00738) and purinergic receptor P2X4 (P2X type 4) (P2X; Genbank Accession No. BC033826), were used as templates; SEQ ID NO: 29 and 30, and SEQ ID NO: 31 and 32 were used as primers for Musc and P2X, respectively; and then PCR was performed (94° C. and 3 min, 94° C. and 1 min, 60° C. and 1 min, 72° C. and 1 min, 25 cycles, then 72° C. and 10 min for GLUT4). The amplified DNAs were cut by the restriction enzyme EcoRV/HindIII, and then each of the thus obtained DNA fragments was inserted into the restriction site (SmaI/HindIII) of pRphi12 and pRphi12TM69, thereby producing human multi-membrane protein expression plasmids.

Example 4

Membrane Protein Expression with Expression Vectors pRphi12 and pRphi12TM69, and Detection by Dot Blots E. coli hosts, BL21 (DE3) and Rosetta (DE3) (Novagen), which contain T7 RNA polymerase, were transformed by using the membrane protein expression plasmids prepared in Example 3. While incubating the transformants, protein expression was induced by using IPTG and, then, the expression rate of each target protein was quantified by dot blot, as follows.

Figure 7:
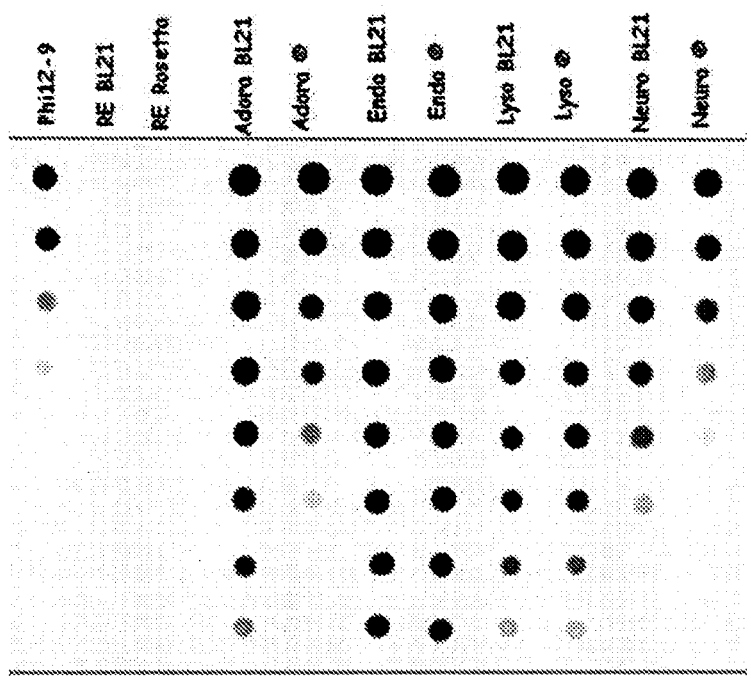
FIGS. 7-9 are the dot blot results for the amounts of expression of A3 adenocine receptor (Adora), endothelin receptor (Endo), lysophosphatidic acid receptor (Lyso), neuropeptide Y receptor (Neuro), serotonin receptor (Sero), thiamine transporter (ThiaT), cysteinyl leukotriene receptor 1 (Leuko), melanocortin 1 receptor (Melano), prostaglandin E receptor (Prost), dopamine receptor D2 (Dopa), muscarinic acetylcholine receptor (Musc), prostaglandin E synthase (mPGES), glucose transporter (GLUT4) and purinergic receptor (P2X) in E. coli BL21 (DE3) (left) and Rosetta (DE3) (right), respectively, all of which are inserted into the expression vector.
Figure 8:
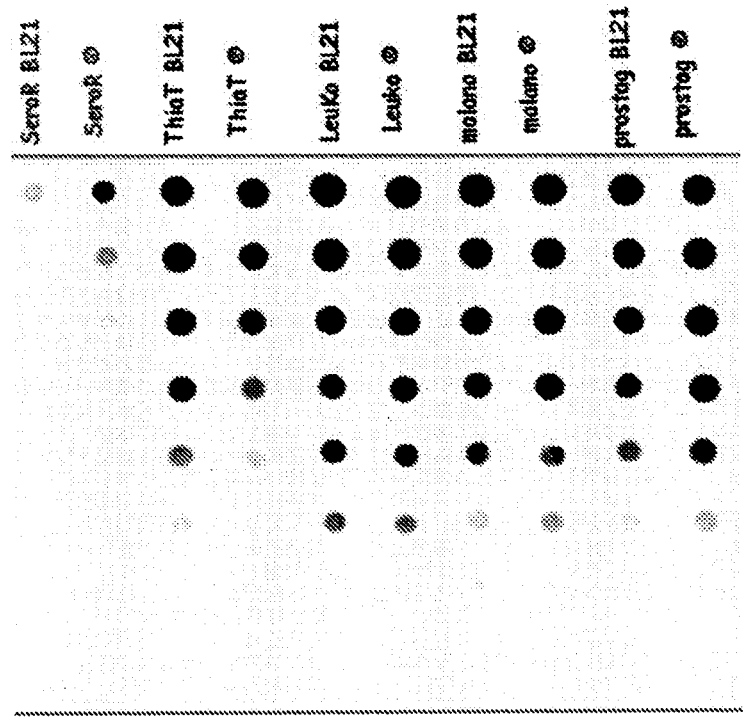
Figure 9:
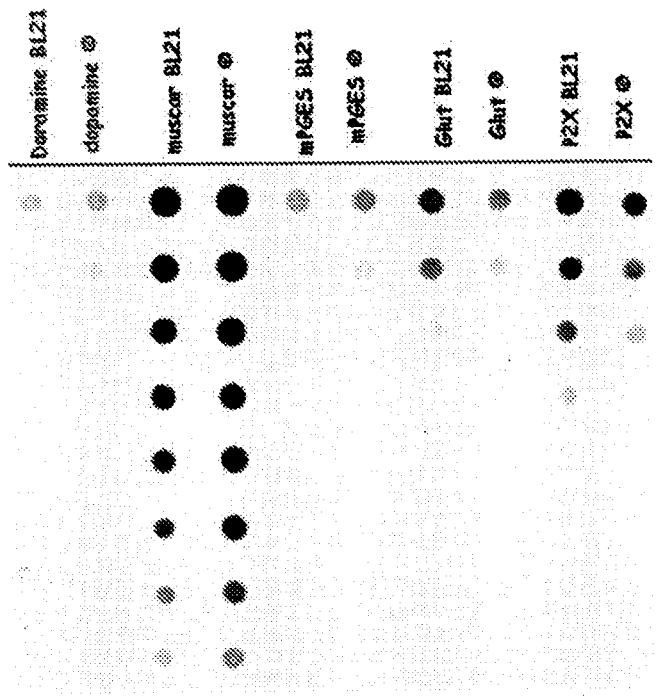

In detail, 100 ng of the P9 proteins of phage phi12, purified in Example 2, was dissolved into a solution and, then, the serial dilutions of the solution (a series of solutions, each of which are half as concentrated (or two times more dilute) than the one from which it was made) were prepared. 1 μl of each of the thus obtained diluted solutions was dropped onto nylon films. Then, each cell which had induced expression of membrane proteins was collected and sonicated, followed by dissolving to a protein concentration of 1 μg/μl. 1 μl of this total protein extract was serially two-fold diluted and, then, each diluted solution was dropped onto nylon film. After the antibody produced in Example 2 was bonded to the nylon film in a ratio of 1:10,000, the bonded antibody was detected by chemiluminescence and the result is shown in FIGS. 7-9. Samples of each target protein was obtained from BL21 (DE3) (left) and Rosetta (DE3) (right).

As shown in FIGS. 7-9, large amount of the target proteins (10 target proteins out of the 14 target proteins, except 4 target proteins (Sero, Dopa, mPGES, Glut)) were detected. Considering that these target proteins are derived from human multimembrane proteins, the results of FIGS. 7-9 indicate that there has been a significant progression in the technical field of membrane protein expression.

Example 5

SDS-PAGEs and Immunoblots of the Expressed Membrane Proteins

Although the dot blot preformed in Example 4 is suitable for measuring the quantity of expression, this method is not appropriate for measuring the quality of expressed proteins, e.g., whether expressed proteins are complete or fragmented. Therefore, in order to examine whether or not the overexpressed proteins are in a normal state, the expressed vectors were transformed into the E. coli hosts, BL21 (DE3) and Rosetta (DE3). Then, while incubating the transformants, protein expression was induced by using IPTG and the expression of each target protein was examined by SDS-PAGE. The detection of the target proteins were carried out by direct observation of protein bands after Coomassie blue staining or by immunoblot using the P9 protein antibody produced in Example 2, and the results are shown in FIGS. 10-12.

Figure 10:
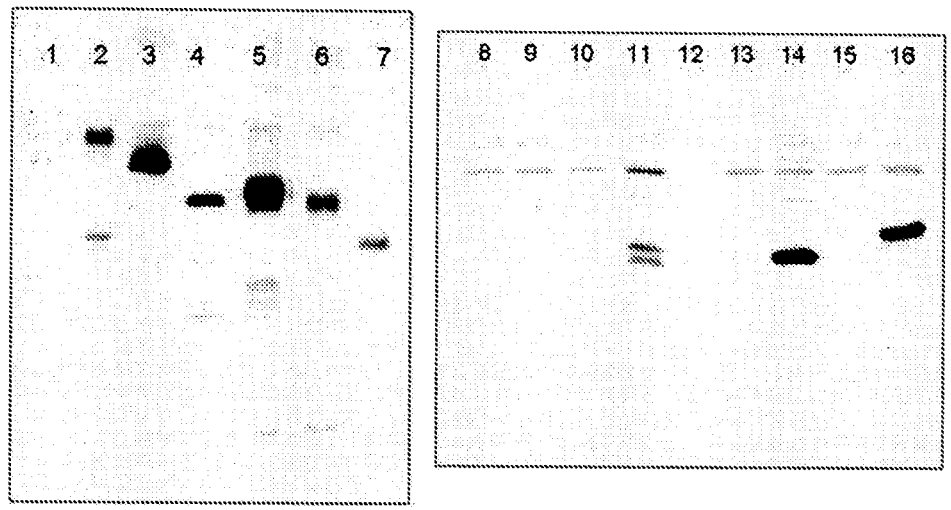
FIG. 10 shows the Western blot results for the amount of expressions of the fourteen proteins, by using P9 antibodies. The expressions of the fourteen proteins were derived by the expression vector pRphi12.

FIG. 10 is the immunoblot results of the proteins expressed by using pRphi12 as a vector. Distinct bands were observed in Sero, Endo, Lyso, Neuro, Leuko, Melano, ThiaT and Prostag. Two bands were appeared in Musc. The size of each protein is corresponding to the size estimated from the amino acid sequence and, thus, these proteins are in a complete form.

Figure 11:
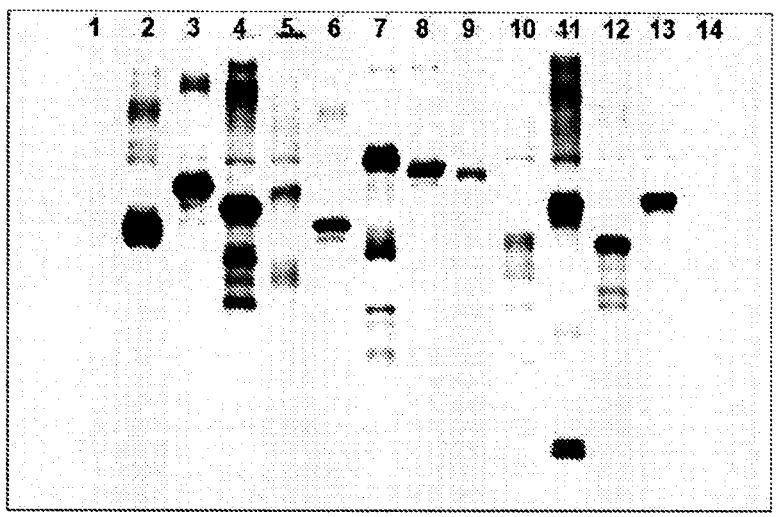
FIG. 11 and FIG. 12 are the detection results of the fourteen proteins, via Western blot with P9 antibody (FIG. 11) and the Coomassie staining (FIG. 12), respectively, which were expressed by using pRphi12TM69 and were followed by SDS-PAGE.

FIG. 11 is the immunoblot results of the proteins expressed by using pRphi12TM69 as a vector. The twelve (12) proteins (Adora, Endo, Lyso, Neuro, ThiT, SeroR, P2X, Dopa, Musc, Leuko, Melano, Prostag) out of the tested 14 proteins were sufficiently expressed.

Figure 12:
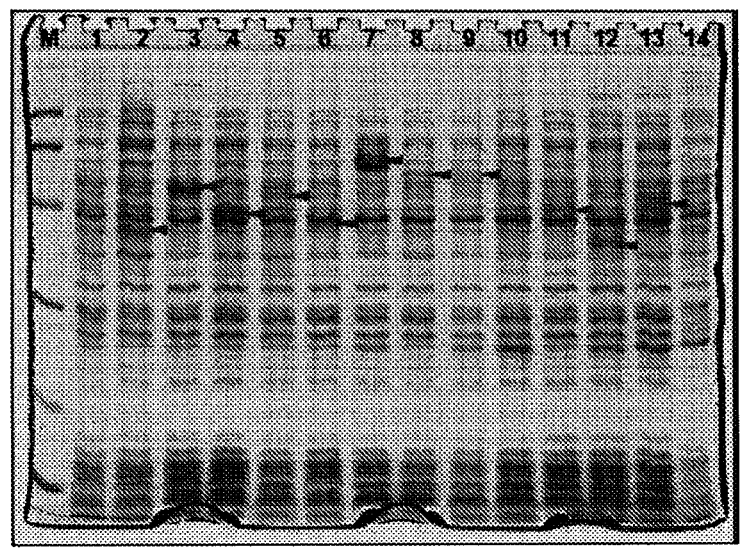

FIG. 12 is the detection results of the proteins expressed by using pRphi12TM69 as a vector, via SDS-PAGE and subsequently the Coomassie staining. As shown in FIG. 12, eleven proteins out of the tested fourteen proteins formed distinct bands.

Example 6

Test of Membrane Protein Folding by GFP Fusion

It is well-known in the art that overexpressed proteins in E. coli often misfold and are present as inclusion bodies. Thus, it was tested whether the membrane proteins expressed according to the present invention are present in cell membranes as is in natural condition, or present in misfolding states, via GFP fusion. When GFP was fused to the C-terminal of sample proteins to be tested, GFP fluorescence was observed if the sample proteins fold into their biochemically functional forms, and vice versa.

Figure 13:
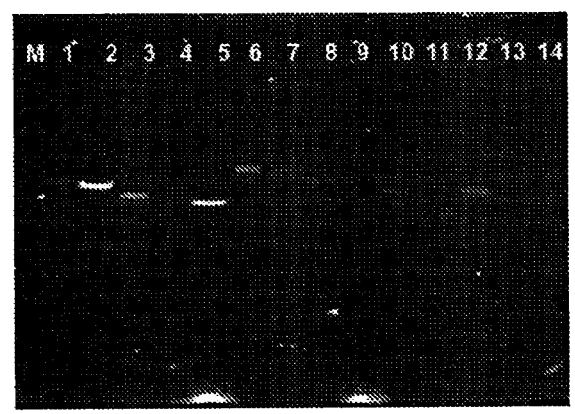
FIG. 13 and FIG. 14 are results of detection of P9-TM-membrane protein-GFP fusion proteins by GFP fluorescence (FIG. 11), GFP antibody (FIG. 14A), and P9 antibody (FIG. 14B), which were obtained by insertion of the membrane proteins and GFP genes into the expression vector pRphi12TM69.
Figure 14:
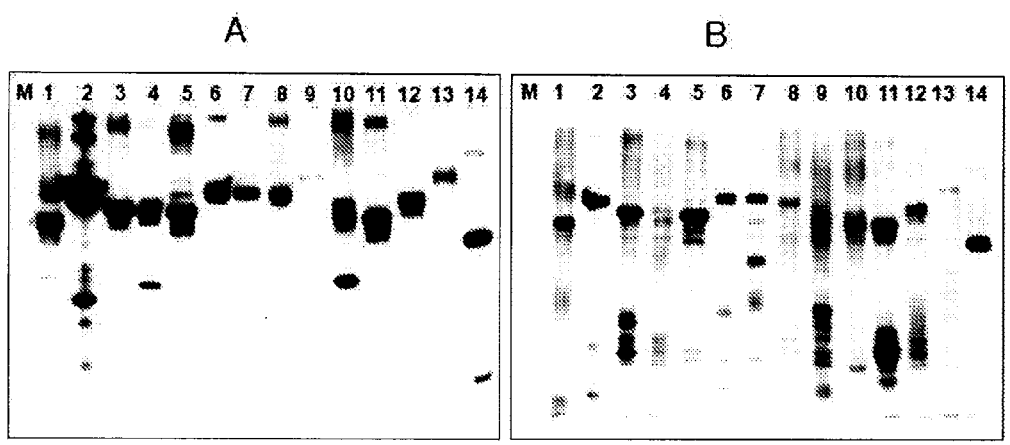

P9-TM-membrane protein-GFP fusion protein was prepared by inserting GFP gene into the C-terminal of the protein inserted to pRphi12TM69. After inducing a T7 promoter, cells were homogenized in order for formation of the proteins. Then, while irradiating the proteins by UV after SDS-PAGE, fluorescence by GFP was observed. Referring to FIG. 13, it can be noted that almost membrane proteins to be tested formed fluorescent bands. In order to examine coincidence between these fluorescent bands and the membrane protein bands, Western blots by using GFP and P9 antibodies were carried out and the results are shown in FIG. 14.

Example 7

Purification of Expressed Proteins

Adora, Endo, Lyso, Neuro, ThiaT, Sero, Leuko, Melano, Prostag and P2X proteins were purified by using the vector of the present invention, after overexpression.

In detail, BL21 (DE3) or Rosetta (DE3) cells, produced in Example 3, which include the expression plasmids of the above-mentioned proteins were incubated in the culture medium (Difco LB broth) at 25° C. until the optical density (O.D.) became 0.8, and then ITPG was added, followed by additional incubation for 6 hr. After collecting the cells, the cell were dissolved in sonication buffer (20 mM Tris-Cl, pH 8.0, 0.3 M NaCl and 10% glycerol) and sonicated. Precipitates were collected after centrifugation of the sonicated solution at 100,000 g for 1 hr. The precipitates were dissolved in sonification buffer containing 39 mM of LDAO, followed by centrifugation at 100,000 g for 1 hr, and the supernatant to which the target proteins were extracted was obtained. Imidazole was added to the supernatant so as to be a concentration of 10 mM and, then, the thus obtained solution was subject to Ni-NTA column chromatography. After sufficiently washing the column with a loading buffer (20 mM Tris-HCl, pH 8.0, 0.3 M NaCl, 10% glycerol and 5 mM imidazole), the target proteins were separated from the column by employing an imidazole concentration gradient (10 mM to 500 mM). The separated proteins were examined by SDS-PAGE and immunoblot and the results are shown in FIG. 15.

Figure 15:
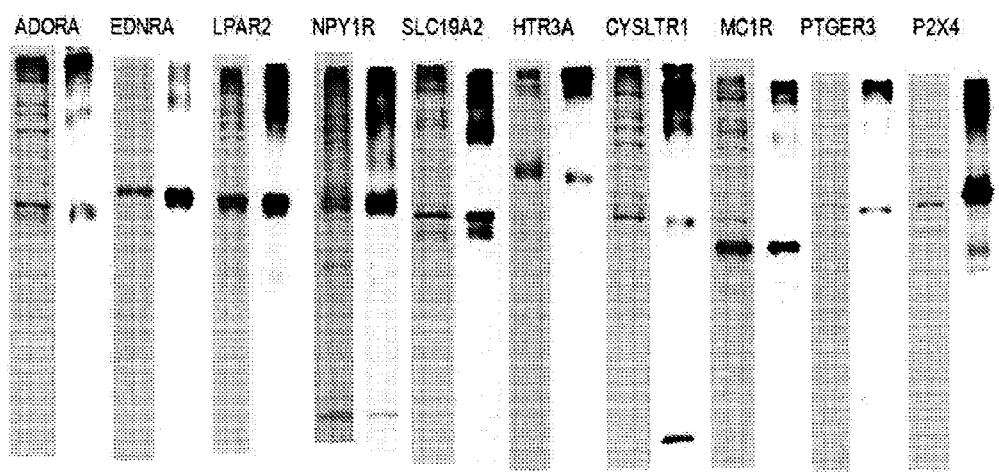
FIG. 15 shows the SDS-PAGE results and the immunoblot results of the overexpressed Adora, Endo, Lyso, Neuro, ThiaT, Sero, Leuko, Melano, Prostag and P2X proteins purified by Ni-NTA column.

As shown in FIG. 15, the ten target proteins were extracted by using a moderate solvent, LADO, followed by Ni-NTA column. Accordingly, the proteins were considerably purified.

The invention claimed is:

1. An expression vector for generating a recombinant major envelope protein, comprising a gene encoding a major envelope protein P9 of Cystovirus phi12, a gene encoding a multicloning site (MCS) for inserting a target membrane protein, and a gene encoding a protease recognition site located between said gene encoding said major envelope protein P9 and said gene encoding said MCS.

2. The expression vector of claim 1, wherein said major envelope protein P9 has the amino acid sequence of SEQ ID NO: 1 or SEQ ID NO: 2.

3. The expression vector of claim 1, wherein said gene encoding said major envelope protein P9 has the base sequence of SEQ ID NO: 3 or SEQ ID NO: 4.

4. The expression vector of claim 1, further comprising a promoter and a gene encoding a histidine tag, wherein said promoter, said gene encoding said major envelop protein P9, said gene encoding said protease recognition site, and said gene encoding said histidine tag, are linked in a 5'- to 3'-direction in the form of being fused to a translational fusion.

5. The expression vector of claim 4, further comprises a gene encoding an extra transmembrane (TM) domain between said gene encoding said major envelop protein P9 and gene encoding said protease recognition site.

6. The expression vector of claim 5, wherein said extra TM domain is derived from a TM domain-containing protein selected from the group consisting of a protein P9 of Cystovirus, a protein P10 of Cystovirus, a major coat protein of *Pseudomonas* phage Pf3 and a major coat protein of Bacteriophage M13.

7. The expression vector of claim 4, wherein said promoter is selected from the group consisting of T7 promoter, T5 promoter and tac promoter.

8. The expression vector of claim 4, wherein said protease is selected from the group consisting of thrombin, Tev and enterokinase.

9. The expression vector of claim 1, wherein said expression vector is pRphi12.

10. The expression vector of claim 5, wherein said expression vector is pRphi12TM69.

11. A cell transformed by the expression vector of claim 1.

12. The cell of claim 11, wherein said cell is a cell of a microorganism or a cell derived from an animal.

13. The cell of claim 11, wherein said cell is *Escherichia coli*.

14. A process for producing a target membrane protein comprising inserting a gene encoding the target membrane protein into the MCS of the expression vector of claim 1, transforming said gene into a cell, and culturing the transformed cell.

15. The process of claim 14, wherein said membrane protein is selected from the group consisting of a membrane receptor, an ion channel, a membrane transporter, a pump, a membrane enzyme, a ligand and a receptor for intercellular communication, a linker for linking cells, a membrane vesicle for intracellular material transport, a ligand and a receptor of endo- and exo-cytosis, a biomembrane protein relating to a viral life cycle, an antibody or a part thereof, and a toxoprotein.

* * * * *